US00PP25648P2

(12) United States Plant Patent
Ludwig

(10) Patent No.: US PP25,648 P2
(45) Date of Patent: Jun. 23, 2015

(54) ***HEUCHERA* PLANT NAMED 'INHEUREDFU'**

(50) Latin Name: *Heuchera×hybrida*
Varietal Denomination: Inheuredfu

(71) Applicant: Walter Ludwig, Heidesheim (DE)

(72) Inventor: Walter Ludwig, Heidesheim (DE)

(73) Assignee: Innovaplant Zierpflanzen GmbH & Co KG, Gensingen (DE)

( * ) Notice: Subject to any disclaimer, the term of this patent is extended or adjusted under 35 U.S.C. 154(b) by 104 days.

(21) Appl. No.: 13/815,478

(22) Filed: Mar. 5, 2013

(51) Int. Cl.
*A01H 5/00* (2006.01)
*A01H 5/02* (2006.01)

(52) U.S. Cl.
USPC ..... Plt./440
CPC ..... *A01H 5/02* (2013.01)

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Burpee *Heuchera,* Dolce Cinnamon Curls Coral bells, like no others. Retrieved on Aug. 20, 2014, retrieved from the Internet at <http://www.burpee.com/perennials/heuchera/heuchera-dolce-cinnamon-curls-prod003422.html> 2 pp.*
Sargent's Gardens. Dolce Cinnamon Curls Coral Bells—New for 2014! Retrieved on Aug. 20, 2014, retrieved from the Internet at <http://search.sargentsgardens.com/12080004/Plant/16500/Dolce_Cinnamon_Curls_Coral_Bells> 4 pp.*

* cited by examiner

*Primary Examiner* — June Hwu
(74) *Attorney, Agent, or Firm* — C. A. Whealy

(57) ABSTRACT

A new and distinct cultivar of *Heuchera* plant named 'Inheuredfu', characterized by its compact and uniformly mounded plant habit; vigorous growth habit; densely foliated and bushy appearance; ruffled dark burgundy-colored leaves that become dark brown with development; and excellent garden performance.

1 Drawing Sheet

Botanical designation: *Heuchera×hybrida.*
Cultivar denomination: 'INHEUREDFU'.

BACKGROUND OF THE INVENTION

The present invention relates to a new and distinct *Heuchera* plant of *Heuchera*, botanically known as *Heuchera×hybrida* and hereinafter referred to by the name 'Inheuredfu'.

The new *Heuchera* plant originated from an open-pollination during July, 2007 in Heidesheim, Germany of *Heuchera×hybrida* 'Peach Flambe', disclosed in U.S. Plant Pat. No. 17,195, as the female, or seed, parent with an unknown selection of *Heuchera×hybrida* as the male, or pollen, parent. The new *Heuchera* plant was discovered and selected by the Inventor as a single flowering plant within the progeny of the stated open-pollination in a controlled greenhouse environment in Heidesheim, Germany in April, 2008.

Asexual reproduction of the new *Heuchera* plant by stem cuttings in a controlled greenhouse environment in Heidesheim, Germany since May, 2008 has shown that the unique features of this new *Heuchera* plant are stable and reproduced true to type in successive generations.

SUMMARY OF THE INVENTION

The new *Heuchera* plant has not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Inheuredfu'. These characteristics in combination distinguish 'Inheuredfu' as a new and distinct *Heuchera* plant:

1. Compact and uniformly mounded plant habit.
2. Vigorous growth habit.
3. Densely foliated and bushy appearance.
4. Ruffled dark burgundy-colored leaves that become dark brown with development.
5. Excellent garden performance.

Plants of the new *Heuchera* differ from plants of the female parent, 'Peach Flambe', in the following characteristics:

1. Plants of the new *Heuchera* are more compact than plants of 'Peach Flambe'.
2. Leaves of plants of the new *Heuchera* are more ruffled than leaves of plants of 'Peach Flambe'.
3. Leaves of plants of the new *Heuchera* are darker and brighter in color than leaves of plants of 'Peach Flambe'.

Plants of the new *Heuchera* can be compared to plants of the *Heuchera* 'Peach Melba', disclosed in U.S. Plant Pat. No. 17,131. In side-by-side comparisons conducted in Heidesheim, Germany, plants of the new *Heuchera* differed primarily from plants of 'Peach Melba' in the following characteristics:

1. Leaves of plants of the new *Heuchera* were more ruffled than leaves of plants of 'Peach Melba'.
2. Plants of the new *Heuchera* and 'Peach Melba' differed in leaf lamina and venation color.

Plants of the new *Heuchera* can be compared to plants of the *Heuchera* 'Caramel', disclosed in U.S. Plant Pat. No.

16,560. In side-by-side comparisons conducted in Heidesheim, Germany, plants of the new *Heuchera* differed primarily from plants of 'Caramel' in the following characteristics:

1. Leaves of plants of the new *Heuchera* were smaller and more ruffled than leaves of plants of 'Caramel'.
2. Leaves of plants of the new *Heuchera* were not as pubescent as leaves of plants of 'Caramel'.
3. Plants of the new *Heuchera* and 'Caramel' differed in leaf lamina and venation color.

BRIEF DESCRIPTION OF THE PHOTOGRAPHS

The accompanying colored photographs illustrate the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph at the bottom of the sheet comprises a side perspective view of a typical plant of 'Inheuredfu' grown in a container.

The photograph at the top of the sheet is a close-up view of a typical plant of 'Inheuredfu'.

DETAILED BOTANICAL DESCRIPTION

The aforementioned photographs and following observations, measurements and values describe plants grown during the autumn in one-gallon containers in an outdoor nursery in Bonsall, Calif. under cultural practices typical of commercial *Heuchera* production. During the production of the plants, day temperatures ranged from 27° C. to 32° C., night temperatures ranged from 20° C. to 24° C. and light levels ranged from 6,000 to 8,000 foot-candles. Plants were four months old when the photographs and the description were taken. In the description, color references are made to The Royal Horticultural Society Colour Chart, 2007 Edition, except where general terms of ordinary dictionary significance are used.

Botanical classification: *Heuchera×hybrida* 'Inheuredfu'.

Parentage:

*Female, or seed, parent.*—*Heuchera×hybrida* 'Peach Flambe', disclosed in U.S. Plant Pat. No. 17,195.

*Male, or pollen, parent.*—Unknown selection of *Heuchera×hybrida*, not patented.

Propagation:

*Type.*—By tissue culture.

*Time to produce a rooted young plant, summer.*—About four to seven weeks at air temperatures ranging from 24° C. to 28° C.

*Time to produce a rooted young plant, winter.*—About five to eight weeks at air temperatures ranging from 18° C. to 21° C.

*Root description.*—Fine, fibrous; white in color.

*Rooting habit.*—Moderately freely branching; medium density.

Plant description:

*Plant and growth habit.*—Herbaceous perennial; basal rosette plant habit with leaves developing from the base; densely foliated and bushy, dense appearance; compact and uniformly mounded plant habit; vigorous growth habit.

*Plant height.*—About 14.4 cm.

*Plant diameter or spread.*—About 43 cm.

Foliage description:

*Arrangement.*—Basal rosette, simple.

*Length.*—About 10.4 cm.

*Width.*—About 8.8 cm.

*Shape.*—Roughly cordate; seven to nine palmately-lobed.

*Apex.*—Broadly obtuse.

*Base.*—Auriculate.

*Margin.*—Crenate with ciliation; ruffled.

*Texture, upper and lower surfaces.*—Sparsely pubescent; slightly rough.

*Venation pattern.*—Palmate; reticulate.

*Color.*—Developing leaves, upper surface: Close to 187B. In the summer, color is closer to darker than 185A. Developing leaves, lower surface: Slightly more grey than 187B. In the summer, color is duller than 187B. Fully expanded leaves, upper surface: Close to 200C becoming closer to N200A with development; venation, close to 187A. In the summer, leaf color is closer to 183B and becoming closer to 183D and 182B with development. Fully expanded leaves, lower surface: Close to 187B becoming closer to 187A with development; venation, close to 187C. In the summer, color is closer to duller than 187B and becoming closer to 187C with development.

*Petiole.*—Length: About 11 cm. Diameter: About 2.5 mm. Texture, upper surface: Sparsely pubescence. Texture, lower surface: Scattered pubescence. Color, upper surface: Close to 187B. Color, lower surface: Close to 183B.

Flower description: Flower initiation and development have not been observed to date on plants of the new *Heuchera*.

Disease & pest resistance: Resistance to pathogens and pests has not been observed on plants of the new *Heuchera* grown under commercial conditions.

Garden performance: Plants of the new *Heuchera* have been observed to have excellent garden performance and to tolerate rain, wind, low temperatures about −6° C. and high temperatures about 30° C.

It is claimed:

1. A new and distinct *Heuchera* plant named 'Inheuredfu' as illustrated and described.

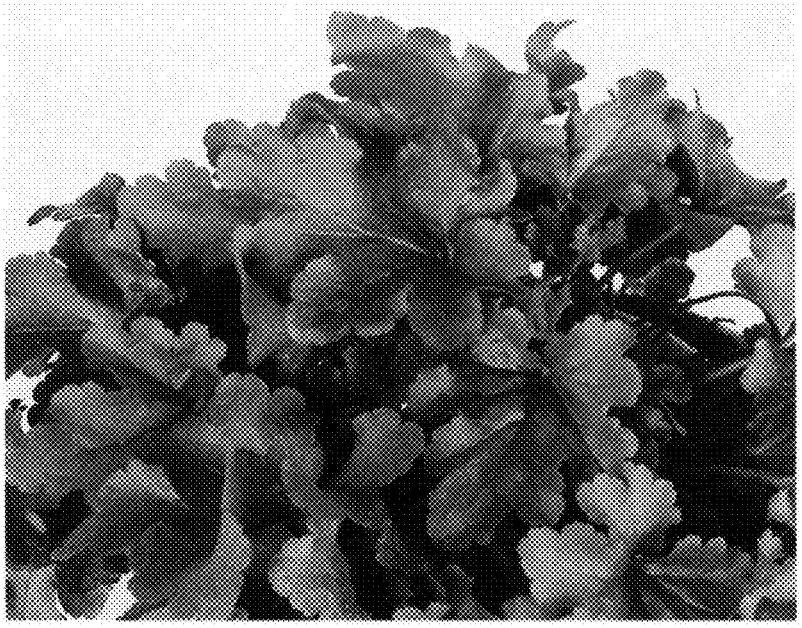
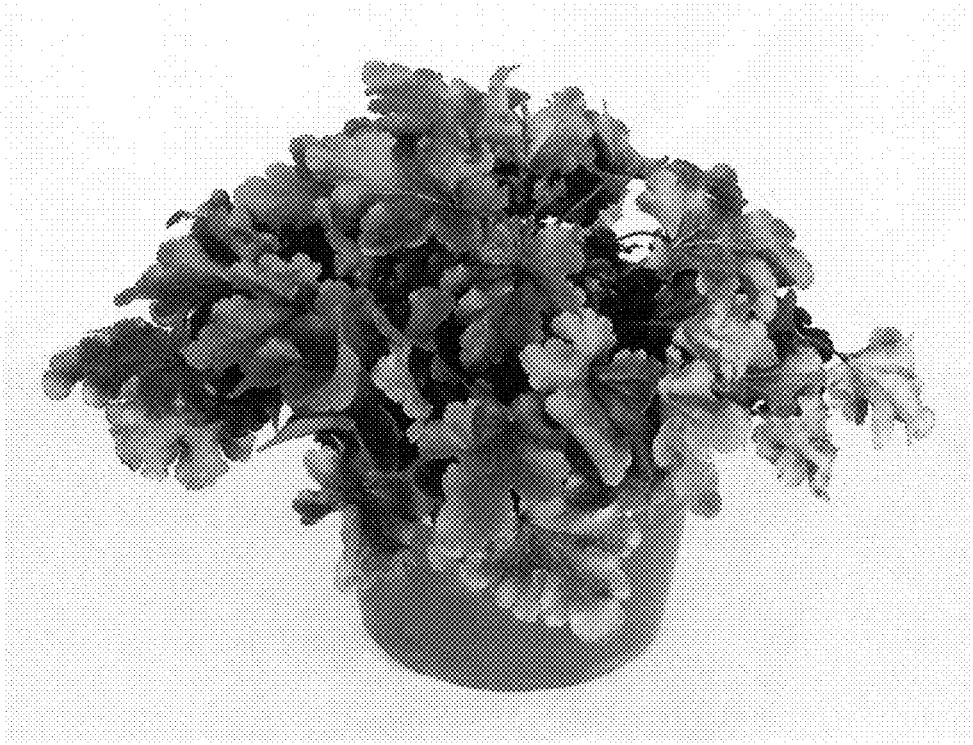

* * * * *